United States Patent [19]

Bahrmann et al.

[11] Patent Number: 5,756,854
[45] Date of Patent: May 26, 1998

[54] PROCESS FOR THE HYDROFORMYLATION OF OLEFINICALLY UNSATURATED COMPOUNDS

[75] Inventors: Helmut Bahrmann, Hamminkeln; Peter Lappe, Dinslaken; Bernhard Fell; Zhigao Xia, both of Aachen, all of Germany; Subba Kanagasabapathy, Pune, India

[73] Assignee: Hoechst Aktiengesellschaft, Germany

[21] Appl. No.: 701,775

[22] Filed: Aug. 26, 1996

[30] Foreign Application Priority Data

Sep. 2, 1995 [DE] Germany .................. 195 32 393.9

[51] Int. Cl.$^6$ .................................................. C07C 45/00
[52] U.S. Cl. .................................... 568/454; 568/17
[58] Field of Search ............................. 568/454, 17

[56] References Cited

U.S. PATENT DOCUMENTS

| | | | |
|---|---|---|---|
| 4,808,756 | 2/1989 | Tokitoh et al. | 568/454 |
| 4,889,957 | 12/1989 | Besson et al. | 568/454 |
| 5,118,867 | 6/1992 | Bahrmann | 568/454 |

FOREIGN PATENT DOCUMENTS

| | | |
|---|---|---|
| 0268268 | 5/1988 | European Pat. Off. . |
| 0407687 | 1/1991 | European Pat. Off. . |
| 2627354 | 12/1976 | Germany . |
| 58216138 | 12/1983 | Japan . |

*Primary Examiner*—Paul J. Killos
*Assistant Examiner*—Jafar Parsa
*Attorney, Agent, or Firm*—Bierman, Muserlian and Lucas

[57] ABSTRACT

A process for the hydroformylation of olefinically unsaturated compounds whose hydroformylation products are insoluble or only sparingly soluble in water, comprising reacting the olefinically unsaturated compounds at 60° to 180° C. and 1 to 35 MPa with carbon monoxide and hydrogen in a homogeneous phase in a polar organic solvent and in the presence of a catalyst system comprising a rhodium carbonyl compound and a salt of a sulfonated or carboxylated organic monophosphine or polyphosphine, which salt is soluble both in the polar organic solvent and in water, distilling off the polar organic solvent from the reaction mixture and separating the catalyst system from the distillation residue by extraction with water.

28 Claims, No Drawings

PROCESS FOR THE HYDROFORMYLATION OF OLEFINICALLY UNSATURATED COMPOUNDS

STATE OF THE ART

Two processes have become established in recent years for the hydroformylation of olefinically unsaturated compounds. One is carried out in a homogeneous phase, i.e. starting olefin, catalyst system (rhodium carbonyl and organic phosphine) and reaction products are present together as a solution and the reaction products are separated by distillation from the reaction mixture. The other process is distinguished by the presence of an aqueous catalyst phase which is separate from the reaction product and comprises rhodium carbonyl and a sulfonated or carboxylated organic phosphine. This variant of the reaction allows the isolation of the hydroformylation products without use of thermal process steps, it simplifies the recirculation of the catalyst and gives a particularly high proportion of unbranched aldehydes when using terminal olefins.

The hydroformylation of higher, olefinically monounsaturated or polyunsaturated compounds is attracting increasing interest. It extends not only to the reaction of hydrocarbons, but also to compounds containing not only double bonds but also further reactive functional groups. An example of such classes of compounds having industrial importance is the unsaturated fatty acid esters which are frequently of natural origin or are prepared from natural raw materials and are available in large amounts. The reaction products of the hydroformylation, monoformylcarboxylic or polyformylcarboxylic esters, which can also contain double bonds which have not yet been reacted, are sought after intermediates which are processed further into widely used products such as polyamines, polyurethanes, alkyd resins, plasticizers and synthetic lubricants.

The hydroformylation of higher, olefinically monounsaturated or polyunsaturated compounds by the homogeneous process using rhodium carbonyl/phosphine catalysts has been studied repeatedly. The economics of this process are only ensured when the homogeneously dissolved catalyst system can be separated without losses of the reaction , products and returned in active form to the hydroformylation reactor. Hitherto, it has only been possible to remove the catalyst from reaction mixtures containing formyl-fatty acid esters derived from the hydroformylation of monounsaturated fatty acid esters. However, the procedure requires complicated measures, in addition the catalyst is obtained in inactive form and the phosphine component of the catalyst system is completely lost [J. Amer. Oil Chem. Soc., Vol. 50, p. 455 (1973)].

When using polyunsaturated compounds having isolated double bonds which are nevertheless close together, the hydroformylation can be carried out with avoidance of double bond isomerization, but the separation and recirculation of the catalyst homogeneously dissolved in the reaction product, for example by distillation, is not possible.

Methyl esters of linoleic and linolenic acids can be hydroformylated in the presence of heterogenized rhodium carbonyl/phosphine complex catalysts based on polysiloxane [Chemiker-Zeitung, Vol. 115 (1991) p. 39 ff]. When using methyl linoleate, the process give monoformylstearyl esters in yields of up to 79%, based on the doubly unsaturated ester used. On hydroformylation in the presence of the catalyst system mentioned, linolenic acid gives a maximum of 50% of diformyl compounds, while triformyl products are obtained at most in subordinate amounts (less than 10%).

The amount of rhodium carried out is on average about 0.5% of the noble metal originally used. It cannot be ruled out that a proportion of the catalyst metal is present in the homogeneous solution in equilibrium with the fixed metal, so that the hydroformylation takes place not only over the fixed bed catalyst, but also in solution.

Difficulties associated with separating reaction product and catalyst system from one another do not occur in the hydroformylation of higher olefinically unsaturated compounds in the presence of an aqueous catalyst solution. However, because of the low solubility of the olefins in water, the conversion is often not satisfactory. This disadvantage can be avoided if, according to EP-B-157 316, the hydroformylation of olefins having more than 6 carbon atoms is carried out in the presence of an aqueous solution comprising rhodium complexes as catalyst and also a quaternary ammonium salt as solubilizer. A further development of this process is the subject matter of EP-B-163 234. According to this patent, olefins of 6 to 20 carbon atoms are reacted with hydrogen and carbon monoxide in the presence of rhodium and the salt of a sulfonated arylphosphine whose cation is a quaternary ammonium ion. The quaternary ammonium salt of the phosphine here acts not only as a catalyst component, but at the same time as a solubilizer. Both processes relate exclusively to the reaction of monounsaturated compounds which contain no functional groups.

OBJECTS OF THE INVENTION

It is an object of the invention to develop a process which allows relatively high molecular weight, olefinically unsaturated compounds to be hydroformylated, with polyunsaturated starting materials being reacted not only partially, but completely to formyl compounds.

It is another object of the invention to provide a hydroformylation process wherein the reaction product and catalyst system can be easily separated from each other and noble metal losses are largely avoided.

These and other objects and advantages of the invention will become obvious from the following detailed description.

THE INVENTION

The novel process of the invention for the hydroformylation of olefinically unsaturated compounds whose hydroformylation products are insoluble or only sparingly soluble in water comprises reacting the olefinically unsaturated compounds at 60° to 180° C. and 1 to 35 MPa with carbon monoxide and hydrogen in a homogeneous phase in a polar organic solvent and in the presence of a catalyst system comprising a rhodium carbonyl compound and a salt of a sulfonated or carboxylated organic monophosphine or polyphosphine, which salt is soluble both in the polar organic solvent and in water, distilling off the polar organic solvent from the reaction mixture and separating the catalyst system from the distillation residue by extraction with water.

The new process combines the characteristics of the hydroformylation in a homogeneous phase with the advantages of the hydroformylation in the presence of a heterogeneous, i.e. aqueous, catalyst phase to provide a new, forward-looking method of operation which is very well suited to reacting relatively high molecular weight olefinically monounsaturated or polyunsaturated compounds. It is used with particular success for hydroformylating esters of unsaturated, preferably polyunsaturated, fatty acids.

Surprisingly, the process of the invention enables a plurality of double bonds present in the ester molecule, which can also be in non-terminal positions, to be simultaneously hydroformylated so that, for example, double unsaturated compounds give diformyl products and triple unsaturated compounds give triformyl products. Furthermore, the new process replaces the heterogeneous reaction system comprising olefinically unsaturated compound and aqueous catalyst solution which is characteristic for the reaction as described in EP-B-167 316 and EP-B-163 234 with a homogeneous solution of starting material and catalyst with the result that the reaction rate is increased and the conversion is improved.

The relatively high molecular weight, olefinically unsaturated compounds suitable as starting materials for the process of the invention have to be soluble in the polar organic solvent used as the reaction medium and have to give hydroformylation products which are insoluble or only sparingly soluble in water. Accordingly, acyclic monoolefins having six or more carbon atoms particularly monoolefins of 10 to 30 carbon atoms such as tri- and tetrabutenes and tri- and tetraisobutenes can be reacted according to the new process.

Polyunsaturated acyclic or cyclic olefins having at least six carbon atoms including, particularly monocyclic and bicyclic olefins, can also be successfully hydroformylated by the process of the invention. Examples of these classes of compounds are dicyclopentadiene, 1,5-cyclooctatriene, 1,5, 9-cyclododecatriene, 1,5-hexadiene, 1,7-octadiene, 1,9-decadiene.

The new procedure is particularly well suited, as mentioned above, for the hydroformylation of unsaturated fatty acid esters. These esters are derived particularly from double or triple unsaturated fatty acids of 8 to 25, preferably from 10 to 20, carbon atoms and from saturated aliphatic monoalcohols of 1 to 10 carbon atoms, preferably methanol. These esters are obtained from natural oils which may, if desired, have previously been refined and distilled, by transesterification. Examples of natural oils as basis for the acid component of the starting ester are cottonseed oil, thistle oil, peanut oil, pumpkin kernel oil, linseed oil, maize oil, soy oil and sunflower oil.

Catalysts used in the process claimed are systems which are soluble in polar organic solvents and in water and comprise a rhodium carbonyl compound as one component and, as a further component, a salt of a sulfonated or carboxylated organic phosphine, which salt is soluble both in water and in the polar organic solvent.

Rhodium carbonyl and phosphine react to form a complex by part of the carbon monoxide molecules in the rhodium carbonyl compound being replaced by phosphine molecules as ligands. The solubility of the rhodium/phosphine complex is here determined by the solubility of the phosphine. Based on rhodium, the phosphine is usually present in excess, i.e. the catalyst system contains not only the rhodium/phosphine complex but also free phosphine.

For the purposes of the present invention, the term "organic phosphines" refers to monophosphines or polyphosphines in which alkyl and/or aryl groups are bonded to the trivalent phosphorous atom or atoms, with at least one of these alkyl and/or aryl groups being singly or multiply sulfonated or carboxylated. Examples of aliphatic groups are straight-chain or branched saturated hydrocarbons of 2 to 8 carbon atoms and cyclic hydrocarbons of 5 to 8 carbon atoms. Typical aromatics are phenyl, benzyl and naphthyl. Both the aliphatics and aromatics can be substituted by further atom groups or atoms such as alkyl, hydroxyl or halogen. The description of organic phosphines also includes those compounds of trivalent phosphorus in which the phosphorus atom is a constituent of a heterocyclic ring.

The phosphines present in the catalyst system do not have to be uniform chemical compounds, but can have different chemical compositions. Thus, they can differ, for example, in the type and bonding of the organic radicals attached to the phosphorus atom, in the degree of sulfonation or carboxylation or in the type of cations. The decisive factor for their suitability as the catalyst constituent is their solubility in water and in polar organic solvents. This criterion is met particularly by salts of sulfonated or carboxylated phosphines whose cation is lithium or an ammonium ion of the formula $N(R^1R^2R^3R^4)^+$. $R^1$, $R^2$, $R^3$ and $R^4$ are individually hydrogen or alkyl, preferably straight-chain or branched alkyl of 1 to 4 carbon atoms.

The anions of the sulfonated or carboxylated monophosphines preferably correspond to the formula

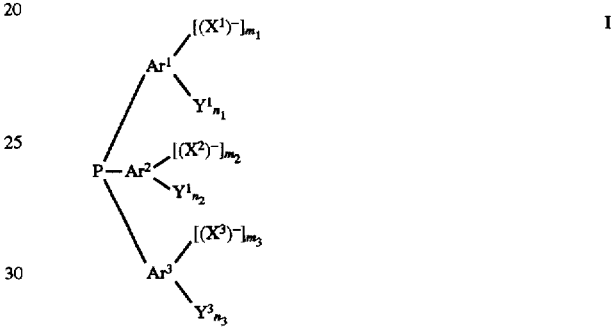

I wherein $Ar^1$, $Ar^2$, $Ar^3$ are individually phenyl or naphthyl, $X^1$, $X^2$, $X^3$ are individually sulfonate ($—SO_3^-$) and/or carboxylate ($—COO^-$), $Y^1$, $Y^2$, $Y^3$ are individually selected from the group consisting of straight-chain or branched alkyl of 1 to 4 carbon atoms, alkoxy, halogen, $—OH$, $—CN$, $—NO_2$ and ($R^5$ and $R^6$)N in which $R^5$ and $R^6$ are individually alkyl of 1 to 4 carbon atoms, $m_1$, $m_2$, $m_3$ are individually integers from 0 to 5, with the proviso that at least one $m_1$, $m_2$ or $m_3$ is greater than 0; $n_1$, $n_2$, $n_3$ are individually integers from 0 to 5.

Particularly suitable salts are derived from the anion of formula I in which $Ar^1$, $Ar^2$, $Ar^3$ are each phenyl and $X^1$, $X^2$, $X^3$ are each sulfonate located in the meta position relative to the phosphorus, i.e. salts of tris(m-sulfonatophenyl) phosphine (abbreviated as TPPTS). Other salts which have been found to be suitable as a catalyst component are those of diphenyl(m-sulfonato-phenyl) phosphine (abbreviated as TPPMS), particularly the lithium salt (Li-TPPMS).

A further group of monophosphine anions which have been found to be suitable as catalyst components are those of the formula

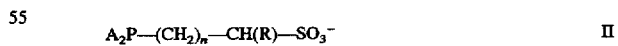

II where the As are individually alkyl and/or aryl, n is 0, 1 or 2 and R is hydrogen or alkyl. The compounds are obtained by sulfalkylation of dialkylphosphines or diarylphosphines with 1,2-, 1,3- or 1,4-sultones

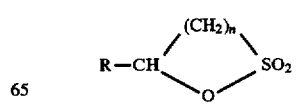

where n = 1, 2 or 3 and R = H, alkyl, e.g. in accordance with

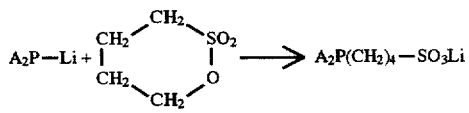

The alkali metal salt can be converted into an ammonium salt by customary methods.

The anion can be formed not only from monophosphines but also from polyphosphines, particularly diphosphines containing at least one sulfonated or carboxylated organic. Diphosphine anions are preferably derived from diaryl compounds of the formula

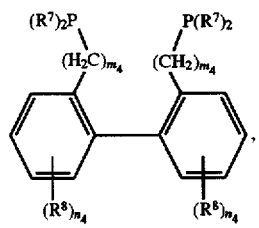   III which are substituted by at least one sulfonate ($-SO_3^-$) or carboxylate ($-COO^-$). In the formula, the $R^7$'s are individually selected from the group consisting of alkyl, cycloalkyl, phenyl, tolyl and naphthyl, the $R^8$s are individually selected from the group consisting of hydrogen, alkyl and alkoxy of 1 to 14 carbon atoms, cycloalkyl, aryl or aryloxy of 6 to 14 carbon atoms and a fused-on benzene ring, the $m_4$s are individually integers from 0 to 5 and $n_4$s are individually integers from 0 to 4.

Preference is given to the sulfonated compounds which can be obtained by conventional methods. Representatives of this class of compounds which have been found to be useful are the products obtained by sulfonation of 2,2'bis(diphenyl-phosphinomethyl) -1,1'-biphenyl or 2,2'-bis (diphenyl-phosphinomethyl)-1,1'-binaphthyl. An example of the anion of a heterocyclic phosphorus compound which may be mentioned is 3,4-dimethyl-2,5,6-tris(p-sulfonatophenyl)-1-phosphanorbornadiene.

The reaction of the olefinically unsaturated starting compounds with hydrogen and carbon monoxide is carried out at temperatures of 60° to 180° C., particularly 100° to 140° C., and at pressures of 1 to 35 MPa. For the hydroformylation of olefins, pressures of from 2 to 35 MPa have been found to be particularly useful and esters of unsaturated fatty acids are preferably reacted at pressures of from 15 to 25 MPa.

The reaction is carried out in a reaction medium comprising a polar organic solvent which dissolves not only the olefinically unsaturated starting compound but also the reaction product and catalyst system. Suitable solvents are low molecular weight aliphatic alcohols of one to four carbon atoms. Instead of pure solvents, it is also possible to use mixtures of two or more of these alcohols such as methanol/ethanol, or methanol/i-propanol mixtures. Reaction media which have been found to be particularly useful are methanol and ethanol which can contain up to 5% by weight of water, but are preferably used in anhydrous form.

The catalyst can be preformed before addition to the reaction system. However, it can be equally successfully prepared in the reaction mixture, i.e. olefinically unsaturated compound and solvent, under reaction conditions from the components rhodium or rhodium compound and the solution of the sulfonated or carboxylated phosphine. Apart from metallic rhodium in finely divided form, it is also possible to use inorganic rhodium salts such as rhodium chloride, rhodium sulfate, rhodium salts of organic acids such as rhodium acetate, rhodium 2-ethylhexanoate or rhodium oxides as rhodium source.

The rhodium concentration in the reaction solution is from 100 to 600 ppm by weight, preferably from 300 to 400 ppm by weight, based on the solution. The phosphine is used in such an amount that at least 20 moles, preferably from 40 to 80 moles, of P(III) are present per mole of rhodium.

The pH of the reaction solution should not go below a value of 3. A pH of 4 to 11 is generally set. When using methanol as solvent, acetylation of the aldehydes formed by hydroformylation can occur. If it is desired to protect the carbonyl from secondary reactions, it is advisable to work at a pH of 4.5 to 6.5, preferably 5.5 to 6.0.

The ratio of carbon monoxide to hydrogen in the synthesis gas can be varied within wide limits. Generally, the synthesis gas used is one in which the volume ratio of carbon monoxide to hydrogen is 1:1 or deviates only little from this value. The reaction can be carried out either batchwise or continuously.

For working up the reaction product, the polar organic solvent is first distilled off. The distillation residue is then washed with water, preferably at ambient temperature, to remove the catalyst system from the aldehydes. This treatment can be repeated a plurality of times, if appropriate. To recover the rhodium completely, it has been found to be advantageous to add a phosphine capable of complex formation with rhodium, advantageously a phosphine which is simultaneously a catalyst component, to the wash water.

In the following examples, there are described several preferred embodiments to illustrate the invention. However, it is to be understood that the invention is not intended to be limited to the specific embodiments.

EXAMPLE 1

A Schlenk tube which has been flushed with argon was charged with 15 ml of methanol, 60 mg (0.05 mmol) of a 8.5% strength by weight rhodium solution (as aqueous $Rh_2(SO_4)_3$ solution) and 700 mg (2 mmol) of diphenyl (lithium 4-sulfonatobutyl)phosphine and the P/Rh molar ratio was 40. The pH of the solution was adjusted to 5 and the solution was introduced by means of a syringe into a laboratory autoclave which had been flushed and filled with argon. 15 g of a 90% strength by weight of methyl linolenate (remainder: methyl linoleate) were placed in the pressure-resistant dropping funnel of the autoclave. The autoclave was flushed with water gas, and a reaction pressure of 20 MPa and a reaction temperature of 120° C. were then set. After a reaction time of one hour, the methyl linolenate was added dropwise and the pressure decrease was monitored via a pressure sensor and a recorder. Gas absorption was complete after 10 hours. The autoclave was cooled, vented and its contents were freed of methanol by distillation under exclusion of air (argon). The residue was washed twice with 15-20 ml each time with oxygen-free water to extract the catalyst system and it was then analyzed. The conversion of linolenic and linoleic esters was quantitative, and the yields were:

5% of monoformyl product based on the total starting materials,

22% of diformyl product based on the total starting materials and

82% of triformyl product based on the proportion of methyl linolenate used in the starting material.

EXAMPLES 2 to 6

Examples 2 to 6 were carried out in a similar manner to Example 1 with variation of the pressure, the pH of the catalyst solution and the P/Rh ratio. The results obtained are shown in Table 1.

TABLE 1

| Ex. | P/Rh | pH | Temp. [°C.] | Pressure [MPa] | Time[1] [h] | MF[2] | DF[3] [mol %] | TF[4] | Conversion [%] |
|---|---|---|---|---|---|---|---|---|---|
| 2 | 40 | 8.4 | 120 | 20 | 3 | 4 | 24 | 80 | 100 |
| 3 | 20 | 5.0 | 120 | 20 | 3 | 14 | 44 | 47 | 100 |
| 4 | 10 | 5.0 | 120 | 20 | 3 | 16 | 44 | 45 | 100 |
| 5 | 10 | 5.0 | 120 | 7 | 3 | 20 | 50 | 34 | 100 |
| 6 | 20 | 5.0 | 120 | 7 | 3 | 15 | 59 | 40 | 100 |

[1]Time after which from 90 to 95% of the gas had been absorbed
[2]Monoformyl product, based on total starting material
[3]Diformyl product, based on total starting material
[4]Triformyl product, based on methyl linolenate used

EXAMPLE 7

A 100 ml V4A stainless steel autoclave which had been flushed with argon and was fitted with a magnetic stirrer, a pressure-resistant metering vessel, a thermocouple support and a pressure sensor (expansion measuring strips) was charged with 24 mg of rhodium (0.05 mmol) as an aqueous $Rh_2(SO_4)_3$ solution and 2.2 g (3 mmol) of tris (tetramethylammonium m-sulfonatophenyl)phosphine dissolved in 30 ml of methanol (P/Rh molar ratio:60). The autoclave was closed, flushed with water gas and a reaction temperature of 120° C. and a reaction pressure of 2 MPa were set. 10 g (50 mmol) of methyl 10-undecenoate were then added from the metering vessel and after 1 hour, the reaction was stopped. 97% of a mixture of 71% of methyl 11-formylundecanoate and 29% of methyl 10-formylundecanoate was formed, as well as 3% of the hydrogenation product, methyl undecanoate. After distilling off the methanol, the catalyst system was taken up in water and separated from the reaction product by phase separation.

EXAMPLE 8

Example 7 was repeated at a reaction pressure of 1 MPa under otherwise identical conditions and conversion was complete after only 30 minutes. Only 1% of methyl undecanoate was obtained in addition to 99% of a mixture of 70% by weight of methyl 11-formylundecanoate and 30% by weight of methyl 10-formylundecanoate. The catalyst system was taken up in water after distilling off the methanol and separated from the reaction product.

EXAMPLE 9

Under argon as a protective gas, 15 ml of methanol, 0.05 mmol of Rh in the form of 60 mg of a 8.5% strength rhodium solution (as aqueous $Rh_2(SO_4)_3$ solution) and 348 mg (1 mmol) of Li-TPPMS (P/Rh molar ratio: 20) were placed in a Schlenk tube. The pH of the solution was adjusted to 6 and the solution was placed in an autoclave under argon. After closing and flushing the autoclave with water gas, a reaction pressure of 10 MPa and a reaction temperature of 120° C. were set. 12 g (60 mmol) of n-tetradec-11-ene were added from a metering vessel and after 1 hour, the olefin had been completely reacted. 98% of a hydroformylation product containing 72% by weight of n-pentadecanal and 28% by weight of 2-methyl-tetradecanal was formed, as well as 2% of the hydrogenation product, n-tetradecane. The aldehydes were mainly (about 70%) obtained in the form of dimethyl acetals. After distilling off most of the methanol solvent, the reaction product was admixed with about 10 ml of water to separate off the catalyst complex. The organic phase was extracted once more with about 5 ml of water. After combining the aqueous extracts, the water was distilled off under reduced pressure and the catalyst system was redissolved in methanol.

EXAMPLES 10 to 15

The catalyst system recovered as described in Example 9 was repeatedly used for the hydroformylation of n-tetradec-1-ene and the conditions were the same as in Example 9. The results of the experiments are shown in Table 2.

TABLE 2

| Example | Conversion (%) | Yield (%) | n-Penta decanal (%) | 2-Methyltetra-decanal (%) | Tetra-decane (%) |
|---|---|---|---|---|---|
| 10 | 100 | 98 | 72 | 28 | 2 |
| 11 | 100 | 96 | 70 | 30 | 4 |
| 12 | 100 | 98 | 71 | 29 | 2 |
| 13 | 100 | 99 | 70 | 30 | 1 |
| 14 | 100 | 98 | 71 | 29 | 2 |
| 15 | 100 | 97 | 70 | 30 | 3 |

EXAMPLE 16

Under argon as a protective gas, 25 ml of methanol, 0.05 mmol of Rh in the form of 60 mg of an 8.5% strength rhodium solution (as aqueous $Rh_2(SO_4)_3$ solution) and 348 mg (1 mmol) of Li-TPPMS (P/Rh molar ratio:20) were placed in a Schlenk tube. The pH of the solution was adjusted to 11 and the solution was placed in an autoclave under argon. After closing and flushing the autoclave with water gas, a reaction pressure of 10 MPa and a reaction temperature of 120° C. were set. 12 g (60 mmol) of n-tetradec-1-ene were added from a metering vessel and after 1 hour, the olefin had been completely reacted. 98% of a hydroformylation product containing 71% by weight of n-pentadecanal and 29% by weight of 2- methyl-tetradecanal was formed, as well as 2% of the hydrogenation product, n-tetradecane. Only 3% of the aldehydes formed were obtained as dimethyl acetals (as a result of the high pH of 11).

EXAMPLE 17

Under argon as a protective gas, 15 ml of methanol, 0.05 mmol of Rh in the form of 60 mg of an 8.5% strength rhodium solution (as $Rh_2(SO_4)_3$ solution) and 348 mg (1 mmol) of Li-TPPMS (P/Rh molar ratio:20) were placed in a Schlenk tube. The pH of the solution was adjusted to 6 and the solution was placed in an autoclave under argon. After closing and flushing the autoclave with water gas, a reaction pressure of 20 MPa and a reaction temperature of 120° C. were set. 16 g (50 mmol) of technical-grade methyl linolenate (55% of methyl linolenate, remainder about 15% of methyl linoleate, about 20% of methyl oleate) were added from a metering vessel and after 3 hours, the olefin was completely reacted. The reaction mixture contained 23% by weight of monoformyl product, 22% by weight of diformyl product and 47% by weight of triformyl product. Based on the proportion of methyl linolenate of 55% in the technical product, this represented a selectivity of 85% based on the formation of the triply hydroformylated product.

Various modifications of the process of the invention may be made without departing from the spirit or scope thereof and it is to be understood that the invention is intended to be limited only as defined in the appended claims.

What we claim is:

1. A process for the hydroformylation of olefinically unsaturated compounds whose hydroformylation products are insoluble or only sparingly soluble in water, comprising reacting the olefinically unsaturated compounds at 60° to 180° C. and 1 to 35 MPa with carbon monoxide and hydrogen in a homogeneous phase in a polar organic solvent and in the presence of a catalyst system comprising a rhodium carbonyl compound and a salt of a sulfonated or carboxylated organic monophosphine or polyphosphine, which salt is soluble both in the polar organic solvent and in water, distilling off the polar organic solvent from the reaction mixture and separating the catalyst system from the distillation residue by extraction with water.

2. The process of claim 1 wherein the olefinically unsaturated compounds are selected from the group consisting of acyclic monoolefins of ten or more carbon atoms, polyunsaturated acyclic and cyclic olefins of at least six carbon atoms and esters of unsaturated fatty acids.

3. The process of claim 1 wherein the olefinically unsaturated compounds are acyclic monoolefins of 16 to 30 carbon atoms.

4. The process of claim 1 wherein the olefinically unsaturated compounds are monocyclic or bicyclic olefins of at least six carbon atoms.

5. The process of claim 1 wherein the olefinically unsaturated compounds are esters of double or triple unsaturated fatty acids of 8 to 25 carbon atoms.

6. The process of claim 5 wherein the esters are of double or triple unsaturated fatty acids of 10 to 20 carbon atoms.

7. The process of claim 2 wherein the esters are derived from saturated aliphatic monoalcohols of 1 to 10 carbon atoms.

8. The process of claim 7 wherein the aliphatic monoalcohol is methanol.

9. The process of claim 1 wherein the polar organic solvent is a low molecular weight aliphatic alcohol of 1 to 4 carbon atoms or a mixture of two or more of these alcohols.

10. The process of claim 9 wherein the polar organic solvent is methanol or ethanol.

11. The process of claim 1 wherein the cation of the salt of the sulfonated or carboxylated organic phosphine, which salt is soluble in polar organic solvent and in water, is lithium or an ammonium ion of the formula $N(R^1R^2R^3R^4)^+$ in which $R^1$, $R^2$, $R^3$ and $R^4$ are individually hydrogen or straight-chain or branched alkyl.

12. The process of claim 11 wherein the alkyl has 1 to 4 carbon atoms.

13. The process of claim 1 wherein the anion of the salt of the sulfonated or carboxylated organic phosphine, which salt is soluble in water and in polar organic solvent, has the formula

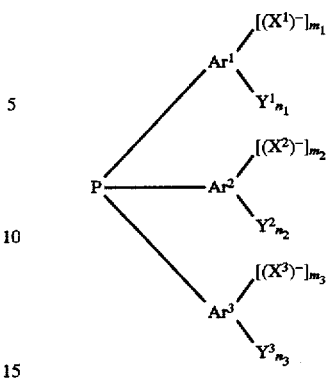

where $Ar^1$, $Ar^2$, $Ar^3$ are individually phenyl or naphthyl, $X^1$, $X^2$, $X^3$ are individually a sulfonate ($-SO_3^-$) and/or a carboxylate ($-COO^-$), $Y^1$, $Y^2$, $Y^3$ are individually selected from the group consisting of straight-chain or branched alkyl of 1 to 4 carbon atoms, alkoxy, halogen, $-OH$, $-CN$, $-NO_2$ and $(R^5R^6)N$ in which $R^5$ and $R^6$ are individually alkyl of 1 to 4 carbon atoms, $m_1$, $m_2$, $m_3$ are individually integers from 0 to 5, with the proviso that at least one $m_1$, $m_2$ or $m_3$ is greater than 0; and $n_1$, $n_2$, $n_3$ are individually integers from 0 to 5.

14. The process of claim 13 wherein the salt of the sulfonated organic phosphine, which salt is soluble in a polar organic solvent and in water, contains the tris(m-sulfonatophenyl) phosphine anion.

15. The process of claim 1 wherein the anion of the salt of the sulfonated organic phosphine, which salt is soluble in a polar organic solvent and in water, has the formula $$A_2P-(CH_2)_n-CH(R)-SO_3^{31},$$

where the As are individually alkyl or aryl, n is 0, 1 or 2 and R is hydrogen or alkyl.

16. The process of claim 1 wherein the anion of the salt which is soluble in a polar organic solvent and in water is derived from diaryl compounds of the formula

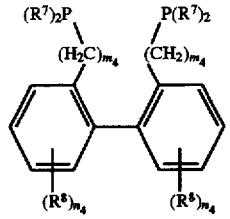

which are substituted by at least one sulfonate ($SO_3^{31}$) or carboxylate ($-COO^{31}$), where, the $R^7S$ are individually selected from the group consisting of alkyl, cycloalkyl, phenyl, tolyl and naphthyl, the $R^8S$ are individually selected from the group consisting of hydrogen, alkyl and alkoxy of 1 to 14 carbon atoms, cycloalkyl, aryl or aryloxy of 6 to 14 carbon atoms and a fused-on benzene ring, the $m_4S$ are individually integers from 0 to 5 and the $n_4S$ are individually integers from 0 to 4.

17. The process of claim 16 wherein the anion of the salt which is soluble in a polar organic solvent and in water is derived from diaryl compounds substituted by at least one sulfonate.

18. The process of claim 1 wherein the reaction of the olefinically unsaturated compounds with hydrogen and carbon monoxide is carried out from 100° to 140° C.

19. The process of claim 5 wherein the reaction of the unsaturated fatty acid esters with carbon monoxide and hydrogen is carried out at from 15 to 25 MPa.

20. The process of claim 1 wherein the rhodium concentration in the catalyst solution is from 100 to 600 ppm by weight, based on the solution.

21. The process of claim 20 wherein the rhodium concentration in the reaction solution is from 300 to 400 ppm by weight, based on the solution.

22. The process of claim 1 wherein at least 20 moles of P(III) are present in the reaction solution per mole of rhodium.

23. The process of claim 1 wherein 40 to 80 moles of P(III) are present in the reaction solution per mole of rhodium.

24. The process of claim 1 wherein the pH of the reaction solution is at least 3.

25. The process of claim 24 wherein the pH of the reaction solution is from 4.5 to 6.5.

26. The process of claim 1 wherein the catalyst system is separated from the distillation residue by a multiple extraction with water.

27. The process of claim 1 wherein a phosphine capable of complex formation with rhodium is added to the water for treating the distillation residue.

28. The process of claim 24 wherein the pH is 4 to 11.

* * * * *